United States Patent
Noda (10) Patent No.: US 9,995,922 B2
(45) Date of Patent: Jun. 12, 2018

(54) ANALYSIS TARGET REGION SETTING APPARATUS

(71) Applicant: SHIMADZU CORPORATION, Kyoto-shi, Kyoto (JP)

(72) Inventor: Akira Noda, Kyoto (JP)

(73) Assignee: SHIMADZU CORPORATION, Kyoto-shi, Kyoto (JP)

(*) Notice: Subject to any disclaimer, the term of this patent is extended or adjusted under 35 U.S.C. 154(b) by 289 days.

(21) Appl. No.: 14/773,057

(22) PCT Filed: Mar. 8, 2013

(86) PCT No.: PCT/JP2013/056538
§ 371 (c)(1),
(2) Date: Sep. 4, 2015

(87) PCT Pub. No.: WO2014/136276
PCT Pub. Date: Sep. 12, 2014

(65) Prior Publication Data
US 2016/0011408 A1   Jan. 14, 2016

(51) Int. Cl.
*G02B 21/36* (2006.01)
*G01J 3/02* (2006.01)
(Continued)

(52) U.S. Cl.
CPC .......... *G02B 21/361* (2013.01); *G01J 3/0275* (2013.01); *G01J 3/108* (2013.01);
(Continued)

(58) Field of Classification Search
CPC .... G02B 21/36; G02B 21/361; G02B 21/365; G01J 3/10; G01J 3/108; G01J 3/0275;
(Continued)

(56) References Cited

U.S. PATENT DOCUMENTS 5,091,964 A * 2/1992 Shimomura ....... G06K 9/00456
358/462
7,831,107 B2 * 11/2010 Dai ........................ G06K 9/342
345/581
(Continued)

FOREIGN PATENT DOCUMENTS

JP   2002310958 A   10/2002
JP   2004220555 A    8/2004
(Continued)

OTHER PUBLICATIONS

Communication dated Mar. 17, 2016, from the European Patent Office in counterpart European Application No. 13876990.6.
(Continued)

*Primary Examiner* — John Lee
(74) *Attorney, Agent, or Firm* — Sughrue Mion, PLLC (57) ABSTRACT

Provided is an analysis target region setting apparatus that can accurately set an analysis target region, based on an observation image of a sample obtained with an optical microscope and the like irrespective of texture on the sample surface when the analysis target region is set therein. The analysis target region setting apparatus according to the present invention divides the observation image into a plurality of sub-regions based on pixel information on each pixel constituting the observation image. Subsequently, consolidation information on each sub-region is calculated, and two adjacent sub-regions themselves are consolidated based on the consolidation information. According to this, it is possible to divide the observation image into sub-regions having similar pixel information with a disregard of noise attributed to the shape of a surface and the like. A user designates one sub-region from among the sub-regions finally obtained, as the analysis target region.

18 Claims, 7 Drawing Sheets

US 9,995,922 B2

Page 2

(51) Int. Cl.
*G01J 3/10* (2006.01)
*G01J 3/453* (2006.01)
*G01N 21/35* (2014.01)
*G06K 9/00* (2006.01)
*G06T 7/00* (2017.01)
*G06T 7/11* (2017.01)
*G06K 9/62* (2006.01)

(52) U.S. Cl.
CPC .............. *G01J 3/453* (2013.01); *G01N 21/35* (2013.01); *G02B 21/365* (2013.01); *G06K 9/0014* (2013.01); *G06K 9/6202* (2013.01); *G06T 7/0004* (2013.01); *G06T 7/11* (2017.01); *G01N 2021/3595* (2013.01); *G06T 2207/10048* (2013.01); *G06T 2207/10056* (2013.01); *G06T 2207/20056* (2013.01); *G06T 2207/30164* (2013.01)

(58) Field of Classification Search
CPC .. G01J 3/453; G01J 2003/4538; G01N 21/35; G01N 2021/3509; G01N 21/359; G01N 2021/3595; G06K 9/0014; G06K 9/00127; G06K 9/6202; G06K 9/6212; G06K 2009/6213; G06T 7/10; G06T 7/11; G06T 7/187; G06T 7/0004; G06T 2207/10048; G06T 2207/10056; G06T 2207/20056; G06T 2207/30164
See application file for complete search history.

(56) References Cited

U.S. PATENT DOCUMENTS

| | | | | |
|---|---|---|---|---|
| 8,396,298 B2* | 3/2013 | Dai | ................... | G06K 9/00456 345/421 |
| 8,401,303 B2* | 3/2013 | Dai | ..................... | G06K 9/32 382/165 |
| 8,401,306 B2* | 3/2013 | Dai | ................... | G06K 9/00456 382/176 |
| 9,100,631 B2* | 8/2015 | Broberg | ................... | H04N 5/91 |
| 2005/0174085 A1* | 8/2005 | Yuri | ..................... | G02B 21/244 318/640 |
| 2005/0180645 A1* | 8/2005 | Hasegawa | .......... | G06K 9/00456 382/239 |
| 2007/0273715 A1* | 11/2007 | Sugiyama | .......... | G02B 27/2214 345/690 |
| 2008/0056610 A1 | 3/2008 | Kanda | | |
| 2009/0310861 A1* | 12/2009 | Lang | ................... | G06F 17/3025 382/173 |
| 2011/0311133 A1* | 12/2011 | Hirota | ................... | G06T 7/0012 382/164 |
| 2013/0322745 A1* | 12/2013 | Lim | ........................ | H04N 9/73 382/162 |
| 2015/0301323 A1* | 10/2015 | Noda | ................... | G01N 21/3563 348/79 |
| 2016/0011408 A1* | 1/2016 | Noda | ..................... | G01N 21/35 250/208.1 |
| 2016/0291306 A1* | 10/2016 | Fukuda | ................ | G02B 21/241 |

FOREIGN PATENT DOCUMENTS

| | | |
|---|---|---|
| JP | 2005296348 A | 10/2005 |
| JP | 2006-208339 A | 8/2006 |
| JP | 2007-130329 A | 5/2007 |
| JP | 2010-276371 A | 12/2010 |

OTHER PUBLICATIONS

International Search Report of PCT/JP2013/056538, dated Apr. 23, 2013. [PCT/ISA/210].
International Written Opinion of PCT/JP2013/056538, dated Apr. 23, 2013. [PCT/ISA/237].

* cited by examiner

ANALYSIS TARGET REGION SETTING APPARATUS

CROSS REFERENCE TO RELATED APPLICATIONS

This application is a National Stage of International Application No. PCT/JP2013/056538 filed Mar. 8, 2013, the contents of all of which are incorporated herein by reference in their entirety.

TECHNICAL FIELD

The present invention relates to an analysis target region setting apparatus which sets an analysis target region within an observed image of a sample obtained with an observation optical system, such as an optical microscope.

BACKGROUND ART

A microspectroscope is an apparatus that includes an observation optical system for microscopically observing a sample surface and an analyzing system for performing a spectroscopic analysis on a part or the whole of an observed area. For example, a microscopic infrared spectroscopic analyzer that performs an analysis with infrared light includes, as the analyzing system, an illumination optical system for emitting infrared light, an aperture for casting the infrared light only on a specific small area of a sample surface, and an infrared detector for detecting light reflected by or transmitted through the sample and passed through the aperture. Hereinafter, the microscopic infrared spectroscopic analyzer is merely referred to as "infrared microscope". The infrared microscope obtains the observation image of visible light on the sample surface by means of the observation optical system, and the position, size, and orientation (angle) of the aperture are set based on the observation image of visible light.

In the infrared microscope, normally a user visually examines the observation image of visible light, and sets the position, size and orientation of the aperture one by one by means of a pointing device such as a mouse. However, when the spectroscopic analysis must be done on a large amount of samples, such as analysis of impurities in the course of product quality management, it is labor and time consuming for a user to manually set the position etc. of the aperture. Accordingly, there has been provided an infrared microscope in which a characteristic image region is extracted from an observation image, and the position etc. of the aperture are automatically set for the region.

For example, Patent Literature 1 discloses an infrared microscope in which an image processing such as edge extraction or binarization is performed based on the hue or illuminance of the observation image of a sample, so as to extract the characteristic image region. Another kind of infrared microscope is known in which when a user designates an appropriate position in the observation image with a pointing device or the like, a region having an illuminance value, for example, in a predetermined range centering on the illuminance value of the designated position is extracted as a characteristic image region.

CITATION LIST

Patent Literature

Patent Literature 1: JP 2010-276371 A

SUMMARY OF INVENTION

Technical Problem

When a sample surface has a rough part, or depressions/projections or the like exist on the sample surface (i.e. when the sample surface has a texture), the reflection or refraction of light on that part is different from that of other part, and the difference develops as difference in hue or illuminance. When a region having the texture is included in a region to be analyzed, these regions are treated as an irregular region (which is referred to as "pseudo irregular region") that should not be included in the characteristic image region in the automatic processing. When many such pseudo irregular regions exist in the region to be analyzed, the characteristic image region is designated excluding the pseudo irregular regions. In that case, the aperture is set not to include the pseudo irregular regions, and the size of the aperture becomes very small, compared with the size of the region to be analyzed. Accordingly, signal intensity obtained with the aperture is reduced to a low level, and the S/N ratio of analytical data deteriorates.

The development of the pseudo irregular regions can be avoided by tuning the settings of a threshold value (for example, "predetermined range"). However, when a large number of different samples are sequentially analyzed, the tuning of the threshold value is required frequently because an optimal threshold value is different depending on the sample, which gives the user a lot of burden.

The aforementioned problem is not limited to the infrared microscope, but generally occurs in an analyzer with which the user sets a region to be analyzed (hereinafter referred to as "analysis target region") based on the observation image of the sample, so as to make an analysis on the analysis target region.

In order to solve the problem, it is an object of the present invention to provide an analysis target region setting apparatus that can accurately set an analysis target region, based on an observation image of a sample obtained with an optical microscope or the like without being affected by the texture on the sample surface when an analysis target region is set.

Solution to Problem

According to the present invention, which is provided in order to solve the problem, an analysis target region setting apparatus is configured to set an analysis target region that is a region analyzed by an analyzer in an observation region of a sample, the analysis target region setting apparatus including:

a pixel information acquisition means configured to acquire pixel information on each pixel constituting the observation region;

a sub-region forming means configured to classify each pixel in accordance with the pixel information and form one sub-region or plural sub-regions composed of pixels that belong to a same classification and are adjacent to each other;

a consolidation information calculating means configured to obtain a characteristic value regarding a part or whole of pixels in each sub-region as consolidation information; and a region consolidating means configured to consolidate the sub-region with one sub-region adjacent to the sub-region based on the consolidation information.

The region consolidating means may consolidate two adjacent sub-regions based on the number of pixels in each sub-region and a difference between a statistic of the pixel information on entire pixels in each sub-region and a statistic of the pixel information on entire pixels in a sub-region adjacent to the sub-region.

Also, the region consolidating means may consolidate two adjacent sub-regions based on the number of pixels positioned on a boundary with the adjacent sub-regions and a statistic of a difference of the pixel information on adjacent pixels on the boundary, in each sub-region.

Furthermore, the region consolidating means may consolidate adjacent sub-regions based on the degree of circularity calculated from the number of pixels in each sub-region and the number of pixels on the boundary between the sub-region and neighboring sub-regions.

The number of pixels in each sub-region corresponds to the area of the sub-region. Also, the number of pixels positioned on the boundary with the adjacent sub-region in each sub-region corresponds to the length of the boundary on which the two sub-regions abut. Furthermore, the number of pixels on the boundary between each sub-region and the surrounding sub-regions corresponds to the length of the circumference (circumferential length) of each sub-region. For example, illuminance, hue, and saturation can be used for the pixel information, and for example, an average value, a median value, and standard deviation can be used for the statistic.

In the analysis target region setting apparatus according to the present invention, first, the image information acquisition means acquires the pixel information based on each pixel in the observation region. The sub-region forming means forms the sub-region made of one pixel or plural adjacent pixels in the observation region based on the pixel information based on each pixel acquired in this way. According to this, in many cases, the observation region is divided into a number of sub-regions. In the present invention, the consolidation information calculating means obtains the characteristic value regarding a part or the whole of pixels in each sub-region as the consolidation information, and the region consolidating means consolidates the adjacent sub-regions themselves based on the consolidation information. The number of pixels, the statistic of the pixel information, and the like are included in "the characteristic value regarding the pixels". For example, "based on the consolidation information" means based on whether or not the consolidation information satisfies a predetermined condition, whether or not the area (the number of pixels) of a certain sub-region is equal to or less than a standard value, whether or not a certain sub-region abuts its adjacent sub-region on almost all the circumference thereof, whether or not the difference between the statistics of the pixel information of the two adjacent sub-regions is equal to or less than a standard value, or the like. As the consolidation information, one characteristic value may be used, or plural characteristic values combined may be employed. With this processing, in the sample in which various pseudo irregular regions such as texture exist, it is possible to eliminate the pseudo irregular regions and consolidate the original region.

It is desirable that the analysis target region setting apparatus according to the present invention include a control means configured to employ the consolidation information calculating means and the region consolidating means plural times. This enables the processing of further consolidating the adjacent sub-regions based on the consolidation information of the sub-regions after the consolidation. It is desirable that the control means can also change the conditions of the consolidation information provided for the region consolidating means to consolidate two adjacent sub-regions. This enables the processing of consolidating the sub-regions while the conditions are being changed.

Subsequently, the user only needs to select the analysis target region to be analyzed by the analyzer from among the plurality of sub-regions finally obtained. In this case, for example, it may be such that the position, size, and orientation of the aperture are automatically set based on the calculation such as optimization for each sub-region to cause the user to select the aperture from among them.

Advantageous Effects of the Invention

In the analysis target region setting apparatus according to the present invention, the sub-region is formed in the observation region based on the pixel information on each pixel in the observation region, and the consolidation information is obtained for each sub-region, and the adjacent sub-regions are consolidated based on the consolidation information. Accordingly, it is possible to divide the observation region into sub-regions having similar pixel information without being affected by noise attributed to the shape, texture or the like of the surface of the sample.

DESCRIPTION OF EMBODIMENTS

An infrared microscope of an embodiment of the present invention will be described referring to drawings.

Embodiments

Figure 1:
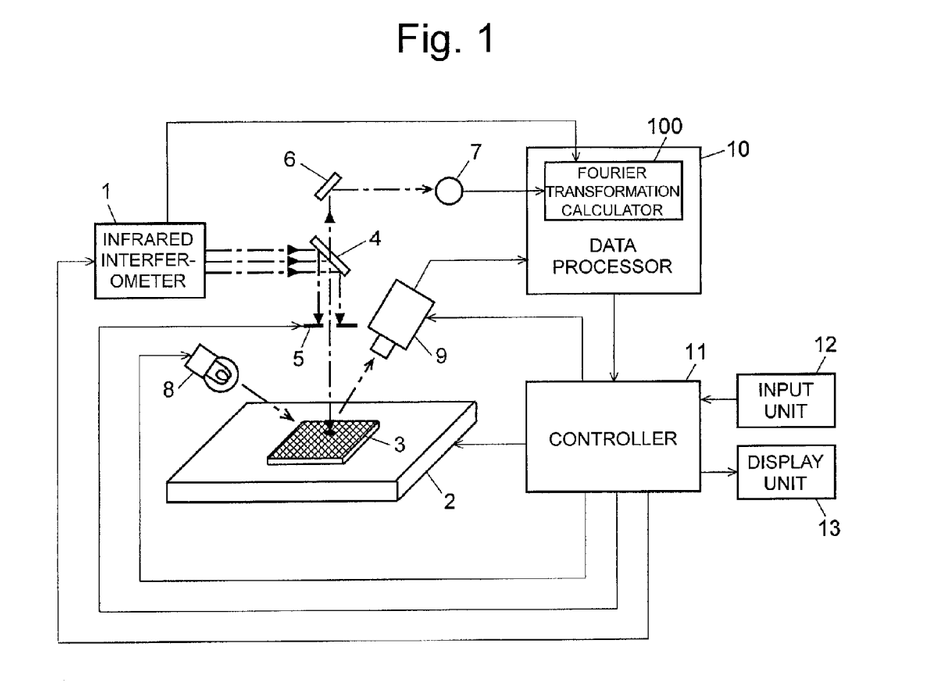
FIG. 1 is a configuration diagram of an essential part of an infrared microscope in an embodiment of the present invention.

FIG. 1 is a configuration diagram of an essential part of the infrared microscope of the present embodiment. In the infrared microscope in the diagram, an infrared interferometer 1 includes an infrared source, a fixed mirror, a moving minor, a beam splitter, and the like, and emits infrared interference light, for which infrared light having a plurality of different wavelengths is interfered. The infrared interference light is reflected by a half minor 4 and cast to a sample 3 placed on a movable stage 2 with an illumination range limited by an aperture 5. The infrared interference light reflected by the sample 3 passes the aperture 5 and half minor 4, and enters an infrared detector 7 through a reflective minor 6, and is detected by the infrared detector 7. When the infrared interference light is reflected on the surface of the sample 3, the infrared interference light is subjected to absorption at wavelengths (generally, multiple wavelengths) unique to a substance existing in its portion. This means that the infrared interference light reached at the infrared detector 7 is one on which the infrared absorption is reflected in a specific region of the sample 3 to which the infrared interference light is cast.

A detection signal from the infrared detector 7 is transmitted to a data processor 10, and a Fourier transformation calculator 100 executes Fourier transformation processing to the detection signal in the data processor 10, so as to obtain an infrared absorption spectrum indicating absorbance in a predetermined range of wavelengths. The obtained spectrum data is transmitted to a controller 11 and displayed on a screen of a display unit 13 connected to the controller 11. Then, visible light emitted from a visible light source 8 is brought into a wide range on the sample 3, and visible reflective light from the sample 3 is introduced to a CCD camera 9. In the CCD camera 9, an observation image of the surface of the sample 3 is generated, and data on the observation image is transmitted to the controller 11. As is the same with the spectrum data, the data on the observation image transmitted to the controller 11 is displayed on the screen of the display unit 13. The controller 11 appropriately controls the movable stage 2 and the aperture 5 to change the region on which the infrared interference light is cast. The controller 11 also controls the operations of respective units such as an infrared interferometer 1 and the visible light source 8.

The data processor 10 and the controller 11 can achieve various functions described later by executing, on a personal computer, dedicated control and data processing software and installed in advance in the personal computer.

The constitution in FIG. 1 is provided to perform a reflective infrared measurement and a reflective visible observation, but may be changed to constitution in which a transmissive infrared measurement is performed, or constitution in which a transmissive visual observation is performed. Also, a mechanism may be incorporated wherein a user directly makes visual observations for the sample surface with an eyepiece.

Figure 2:
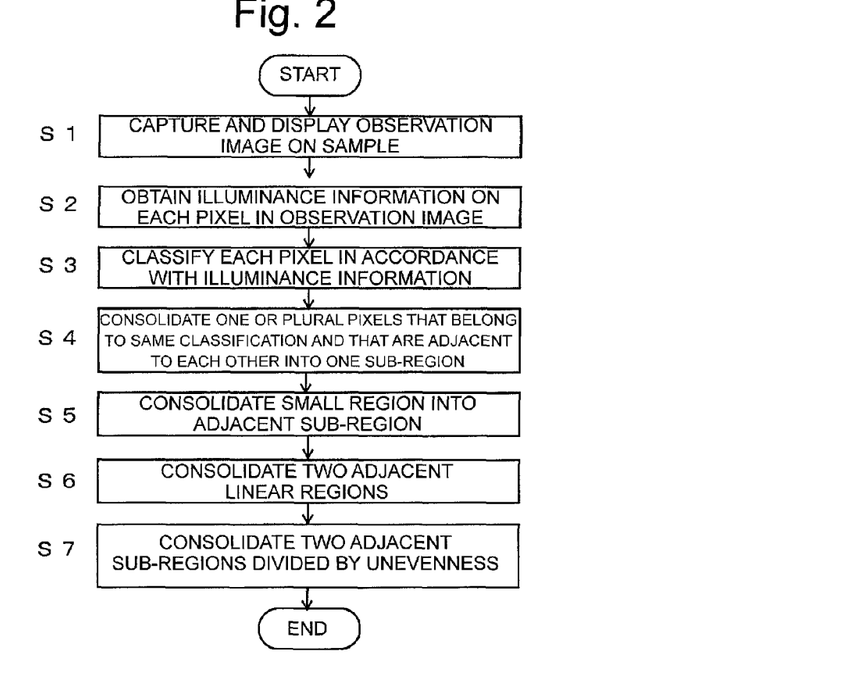
FIG. 2 is a flowchart illustrating a procedure of setting an analysis target region in the infrared microscope in the present embodiment.

Next, a procedure that the controller 11 sets the analysis target region based on observation image data in the infrared microscope in the present embodiment will be described referring to flowchart in FIG. 2.

Figure 6:
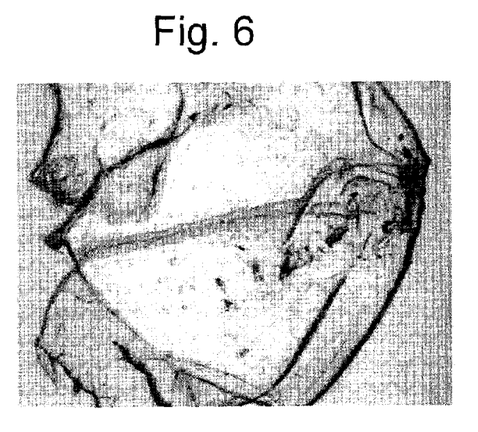
FIG. 6 is a diagram illustrating one example of an observation image displayed on a screen of a display unit.

When the sample 3 to be measured is placed on the movable stage 2, first, a visible image of the sample 3 is taken by the CCD camera 9, and data on the image is transmitted to the controller 11, and an observation image as illustrated in FIG. 6 is displayed on the screen of the display unit 13 (Step S1). The controller 11 obtains illuminance information on each pixel constituting the observation image as pixel information (Step S2). It is noted that hue, saturation, and the like other than the illuminance can be appropriately used for the pixel information.

The sub-region forming processing is performed in steps S3 and S4. In the sub-region forming processing, each pixel constituting the observation image is classified in accordance with the illuminance information thereof, and one pixel or plural pixels that belong to the same classification, and that are adjacent to each other are consolidated into one sub-region. According to the processing, a plurality of sub-regions are formed in the observation image.

When the number of sub-regions obtained in the sub-region forming processing is large, subsequent computation is enormously complicated. In this case, the number of classifications of the pixels in Step S3 is reduced. This reduces the number of sub-regions obtained in Step S4, so that the computation can be simplified.

The processing in Steps S3 and S4 can be easily performed, for example, by low-gradation processing. When the number of sub-regions obtained in Step S4 increases to the extent that a problem occurs in terms of a subsequent processing time, the number of gradations is reduced, and the same processing is repeated.

In steps S5 to S7, the processing of consolidating a sub-region that should be naturally included in an adjacent sub-region (this sub-region to be included may be referred to as "pseudo irregular region"), among the plurality of sub-regions formed in Steps S3 and S4, into the adjacent sub-region is performed.

In Step S5, small region consolidating processing is performed in which a small pseudo irregular region generated by rough part, depressions/projections, or the like existed on the sample surface is consolidated with the sub-region adjacent to it. The small region consolidating processing will be described in detail referring to a flowchart in FIG. 3.

Figure 3:
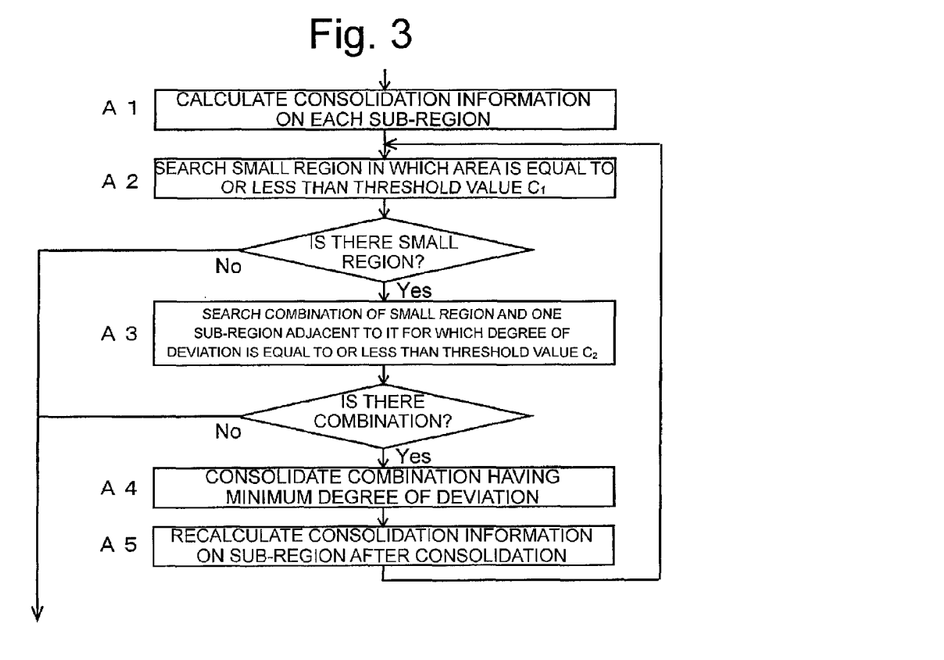
FIG. 3 is a flowchart illustrating a procedure of small region consolidating processing in the infrared microscope in the present embodiment.

In the small region consolidating processing, first, consolidation information on each sub-region formed in the observation image is calculated (Step A1). In the present embodiment, the number of pixels (area) in the sub-region, the sum of illuminance in the sub-region, the sum of the squared values of the illuminance, the length of the boundary with one sub-region adjacently disposed, and the sum of illuminance difference on its boundary are used as the consolidation information. Regarding the consolidation information, when two sub-regions are consolidated, the consolidation information of the sub-regions after the consolidation can be calculated only by adding respective pieces of consolidation information, and therefore high-speed calculation is enabled. Also, average illuminance in the sub-region, standard deviation, an average illuminance difference on the boundary with one sub-region adjacently disposed, the entire length of the boundary (the length of circumference), and a degree of circularity (a value obtained by dividing the area by the length of circumference) are indirectly calculated based on the consolidation information. The length of the boundary with one sub-region adjacently disposed or the entire length of the boundary can be calculated based on the number of pixels positioned at the boundary.

Subsequently, all the small regions in which the area obtained in Step A1 is equal to or smaller than a threshold value $C_1$ is searched (Step A2). For all small regions, the combination of a small region i and one sub-region j adjacent to it, for which a degree of deviation $f_{ij}$ is equal to or lower than a threshold value $C_2$ are searched in Step A2 (Step A3).

$$f_{ij}=|(R_i-R_j)\times B_{ij}|$$

$R_i$ and $R_j$ respectively represent the average illuminance of the sub-regions i and j, and $B_{ij}$ represents the average illuminance difference on the boundary between the sub-regions i and j. Then, the combination of the two sub-regions having the minimum degree of deviation $f_{ij}$ is consolidated from among all the combinations obtained in Step A3 (Step A4). When the sub-regions are consolidated, the consolidation information on the sub-region after the consolidation is changed, and therefore the consolidation information on the sub-region after the consolidation is recalculated (Step A5), and the processing in Steps A2 to A4 is performed again. The processing above is repeated until the combination of the two sub-regions to be consolidated in Step A4 is no longer searched in Steps A2 and A3.

It is noted that Step A2 may apply the processing of searching a combination that the length of the boundary between the small region i and the sub-region j adjacent to the small region i is equal to or higher than a certain standard value. This means that, when the small region surrounded by its adjacent sub-regions exists, the consolidation can be made, even when a difference in average illuminance or a difference in average illuminance difference therebetween is large. This processing may be added between Step A2 and Step A3.

In Step S6, linear region consolidating processing of consolidating linear illuminance unevenness is performed. When a plurality of substances exist in the sample, the pseudo irregular region having the linear illuminance unevenness often emerges due to a difference in level or the like on the boundary between the substances, and therefore a plurality of linear sub-regions often emerge contiguously. For this reason, the aim of the linear region consolidating processing is the consolidation of these. Hereinafter, the linear region consolidating processing will be described in detail referring to a flowchart in FIG. 4.

Figure 4:
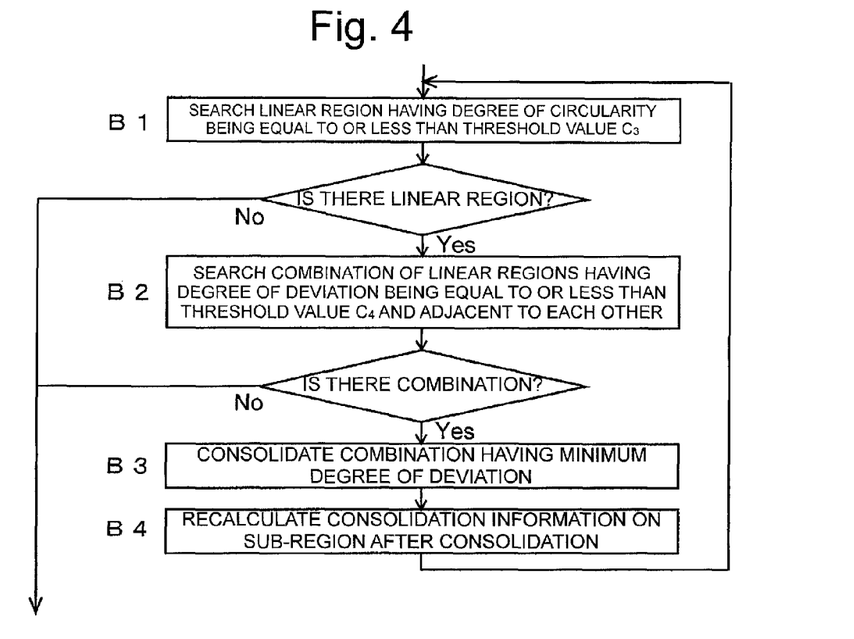
FIG. 4 is a flowchart illustrating a procedure of linear region consolidating processing in the infrared microscope in the present embodiment.

In the linear region consolidating processing, first, all the linear sub-regions, in which the degree of circularity obtained based on the consolidation information is equal to or lower than a threshold value C3, are searched (Step B1). Subsequently, the combinations of two linear regions that are adjacent to each other and have the degree of deviation fij being equal to or lower than a threshold value C4 are searched from among the linear regions searched in Step B1 (Step B2). A combination having the minimum degree of deviation fij is consolidation target, from among all the combinations obtained in Step B2 (Step B3). After the two linear regions are consolidated, as is the same with the small region consolidating processing, the consolidation information on the consolidated linear region (sub-region) is recalculated (Step B4), and the processing in Steps B1 to B3 is performed again. The processing above is repeated until the combination of the linear regions is no longer searched in Steps B1 and B2.

It is noted that, in Step B1, the linear region may be extracted by use of a degree of linearity calculated based on Hesse matrix. Also, Step B2 may employ the processing of searching a combination of the linear regions i and j of which the length of the boundary between the two adjacent linear regions is equal to or higher than a certain standard value. Also, the processing may be performed after the search of the combination of the two linear regions being equal to or lower than the threshold value $C_4$.

In Step S7, illuminance unevenness consolidating processing is performed. When the pseudo irregular region caused by unevenness such as illuminance unevenness and color unevenness emerges on the sample surface, the sub-regions excessively emerge. For this reason, in Step S7, the sub-regions divided by the unevenness are consolidated. The illuminance unevenness consolidating processing will be described in detail referring to FIG. 5.

Figure 5:
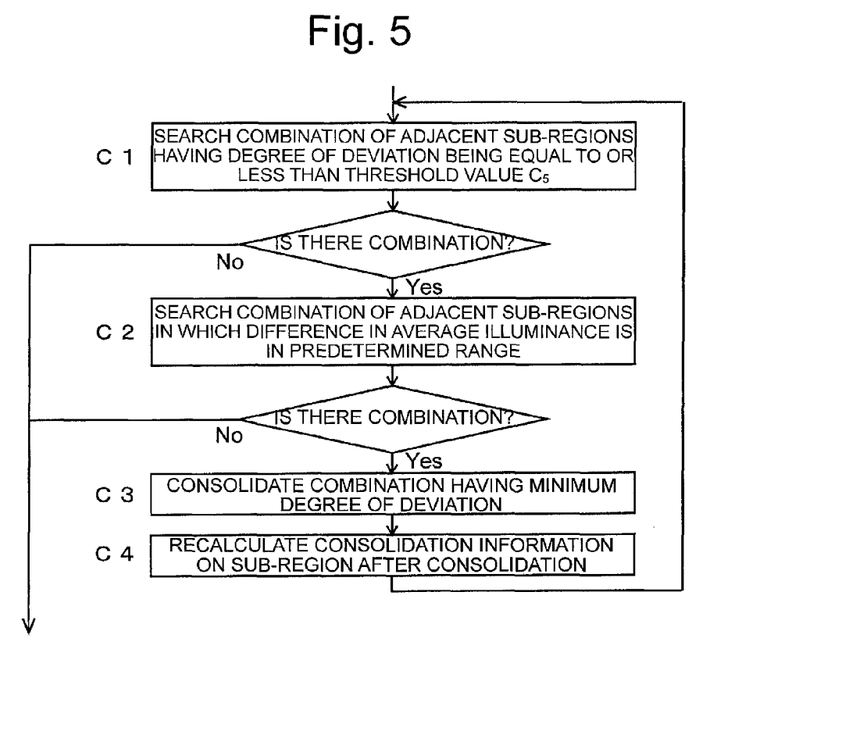
FIG. 5 is a flowchart illustrating a procedure of illuminance unevenness consolidating processing in the infrared microscope in the present embodiment.

In the illuminance unevenness consolidating processing, first, a combination of two adjacent sub-regions having the relatively long length of the boundaries adjacent to each other and the degree of deviation $f_{ij}$ being equal to or lower than a threshold value $C_5$ is searched (Step C1). Subsequently, a combination of the two sub-regions i and j that satisfy the condition below is searched by use of the average illuminance and the standard deviation obtained based on each piece of consolidation information, among the combinations searched in Step C1 (Step C2).

$$|R_i-R_j|\le\alpha\times\min(D_i,D_j)$$

Herein, $\alpha$ represents a positive integer, and $D_i$, and $D_j$ respectively represent the standard deviation of the sub-regions i and j. The two sub-regions having the minimum degree of deviation $f_{ij}$ are consolidated, from among the combinations obtained in Step C2 (Step C3). As described above, after the two sub-regions are consolidated, the consolidation information on the post-consolidation sub-region is recalculated (Step C4), and the processing in Steps C1 to C3 is performed again. The processing above is repeated until the combination of the two sub-regions is no longer searched in Steps C1 and C2.

As described above, in the analysis target region setting apparatus in the present embodiment, the controller 11 can consolidate the pseudo irregular region having various patterns into the sub-regions in its periphery by changing the consolidation condition at a predetermined timing. It is noted that various conditions may be added to the consolidation condition in accordance with the types of the pseudo irregular region as long as the consolidation information on each sub-region is used. Also, any information may be added to the consolidation information as long as information obtained based on each sub-region is used.

Hereinafter, effect given by the processing at each step relative to the observation image in FIG. 6 is described. The image in FIG. 6 shows a resin piece under transmissive observation. Also, FIGS. 7 to 11 show images of which sub-regions obtained by each processing described later and classified by color are displayed.

Figure 7:
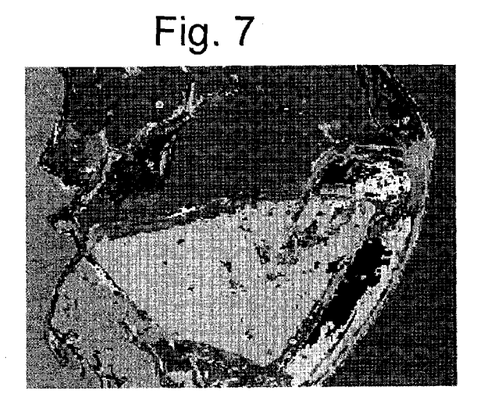
FIG. 7 is a diagram of regions obtained by the sub-region forming processing and classified by color, and displayed.

FIG. 7 is a diagram illustrating the result after the sub-region forming processing in Step S4 is performed for the observation image in FIG. 6. As illustrated in the diagram, large amount of noises due to texture occur in only the processing in Step S4.

Figure 8:
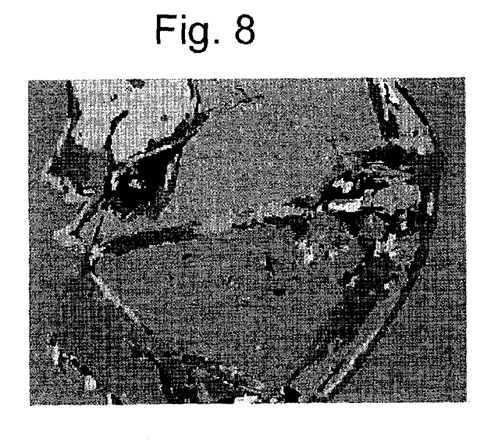
FIG. 8 is a diagram of each region obtained without performing the small region consolidating processing, classified by color, and displayed.

FIG. 8 shows the result when the small region consolidating processing in Step S5 is not performed (Steps S6 and S7 are performed). As illustrated in the diagram, when the small region consolidating processing is not performed, a large number of minute pseudo irregular regions remain. Also, the boundary line at a boundary section is unclear, which leads to a side effect such as the oversight of a streak on the horizontal line around the center.

Figure 9:
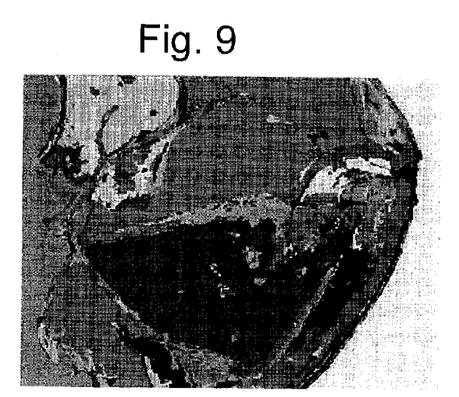
FIG. 9 is a diagram of each region obtained without performing the linear region consolidating processing, classified by color, and displayed.

FIG. 9 shows the result when the linear region consolidating processing in Step S6 is not performed (Steps S5 and S7 are performed). In FIG. 9, the linear regions are not consolidated, and therefore fine sub-regions that are not fully consolidated remain on the boundary or linear texture portions.

Figure 10:
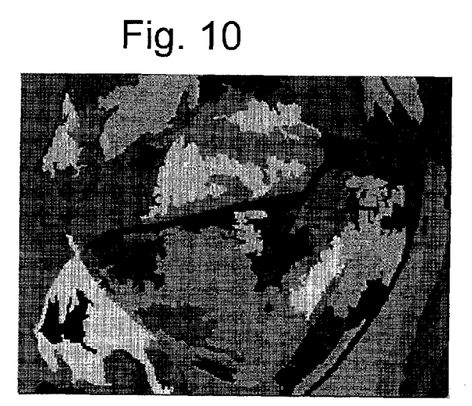
FIG. 10 is a diagram of each region obtained without performing the illuminance unevenness consolidating processing, classified by color, and displayed.

FIG. 10 shows the result when the illuminance unevenness consolidating processing in Step S7 is not performed (Steps S5 and S6 are performed).

Figure 11:
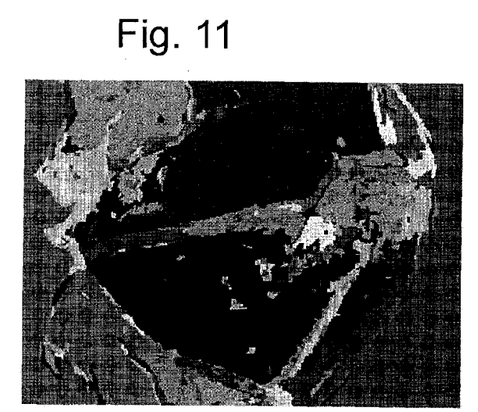
FIG. 11 is a diagram of each region obtained by performing the entire region consolidating processing, classified by color, and displayed.

FIG. 11 shows the result when the entire processing in Steps S1 to S7 is performed. In view of the result in FIG. 11, it is noticeable that minute texture is consolidated into the surrounding sub-region, and a large number of sub-regions are not formed on the boundary or linear texture portions.

Figure 12:
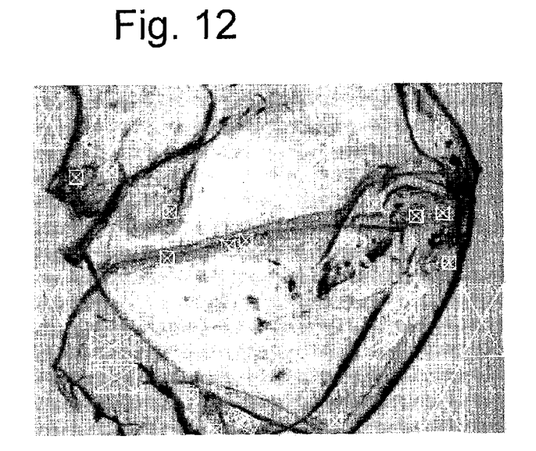
FIG. 12 is a diagram illustrating an aperture candidate set in each region.

FIG. 12 is a diagram illustrating aperture candidates, which are set by the controller 11 with respect to each sub-region obtained in FIG. 11, when analysis is made with the infrared microscope. In the infrared microscope in the present embodiment, a plurality of aperture sizes and inclinations that may be actually set are prepared, and these apertures are fitted for each sub-region for selection of an optimal aperture.

It is noted that, in the present embodiment, when two apertures can be set based on the identical aperture size and angle in each region to determine whether or not each sub-region is appropriately divided, the two apertures can be set accordingly so as to compare the analytic results of the two apertures. Also, when the settings cannot be made in this way, only one aperture is set in each region. In the present embodiment, the apertures have been fitted with an aperture set in which squares or rectangles having an appropriate size are tilted in 16 directions.

Figure 13:
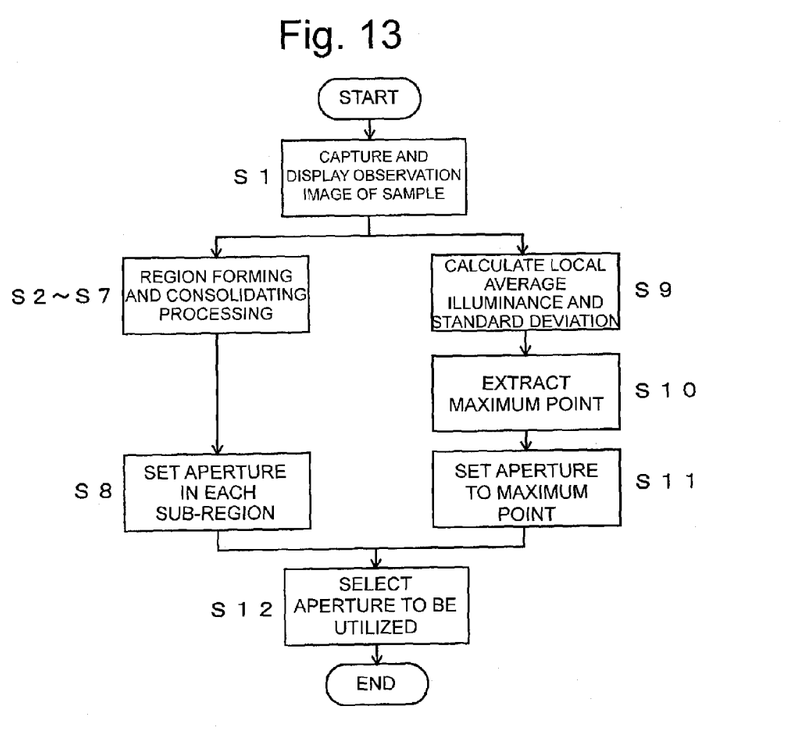
FIG. 13 is a flowchart illustrating another procedure of setting the analysis target region of the infrared microscope in the present embodiment.

FIG. 13 is a flowchart illustrating another procedure of setting the analysis target region in the infrared microscope in the present embodiment. In the processing, maximum point extraction processing (Steps S9 and S10) is parallelly performed along with the region forming and consolidating processing (Steps S2 to S7), and the user selects which aperture to be used (Step S12), from among the aperture candidates (Steps S8 and S11) obtained through the two processing described above.

In Step S9, average and standard deviation calculating processing is performed. In this processing, the average value of local characteristics (the illuminance value in the present embodiment) and the standard deviation of the observation image are calculated, so as to calculate an a value. In the present embodiment, first, an image in which only an abnormal point is bright (or dark) is generated by cutting a low-frequency component to enhance the speed of the processing.

Subsequently, "robust average and standard deviation calculating processing" is performed against an abnormal value (a value at the abnormal point). A general technique may be employed for "robust average and standard deviation calculating processing", but, in the present embodiment, a normal average value and a standard deviation value inclusive of an abnormal value are calculated, and the processing of calculating the average value and the standard deviation value exclusive of the abnormal value is repeated in a range of $\pm 1\alpha$ from the average value thereafter.

In Step S10, maximum point searching processing is performed. In this processing, a point, at which the $\alpha$ value obtained in Step S9 is equal to or greater than a threshold value $C_6$ and reaches maximum when locally viewed, is searched.

In the present embodiment, the threshold value $C_6$ is dynamically determined so as to search the maximum points in accordance with only the number of required apertures (that is, the threshold value $C_6$ is changed in a way that the number of maximum points searched in the maximum point searching processing reaches a predetermined number).

Figure 14:
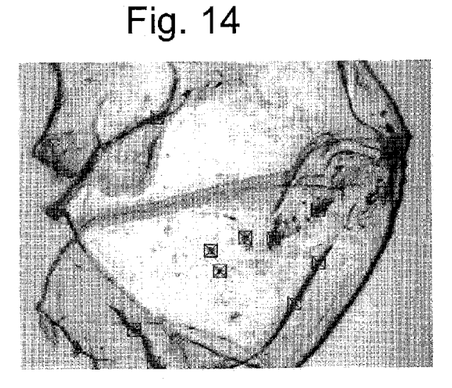
FIG. 14 is a diagram illustrating an aperture candidate set to each maximum point.

FIG. 14 is a diagram illustrating that the aperture is set to each maximum point searched in Step S10. As illustrated in the diagram, a minute point that is likely to be removed as noise in the region forming and consolidating processing in Steps S2 to S7 is extracted in the maximum point extraction processing in Steps S9 and S10. For this reason, the processing in Steps S9 and S10 can be performed as complementary processing for the region forming and consolidating processing in Steps S2 to S7.

Figure 15A:
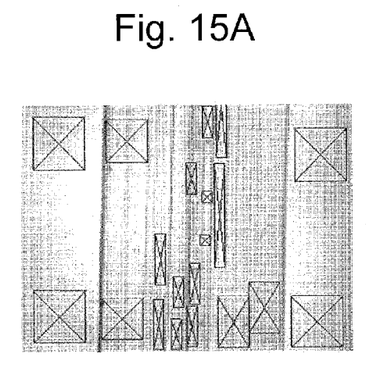
FIG. 15A is a diagram illustrating the aperture candidates set to another observation image after the region consolidating processing.
Figure 15B:
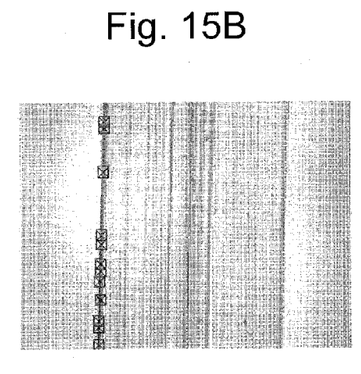
FIG. 15B is a diagram illustrating the aperture candidates set to another observation image after the maximum point extraction.

FIG. 15A is a diagram illustrating the aperture candidates set in Step S8 after the region forming and consolidating processing in Steps S2 to S7, and FIG. 15B is a diagram illustrating the aperture candidates set in Step S11 after the maximum point extraction processing in Steps S9 and S10. In the used observation image, the sub-region emerges in striped patterns, and the apertures can be appropriately set for the each of sub-regions by use of the region forming and consolidating processing. On the other hand, the apertures set after the maximum point extraction processing emerge only on the boundary portion of the observation image. As shown in FIG. 15B, the region forming and consolidating processing is suitable for the sample in which the areas having a similar illuminance value relatively widely emerge.

Figure 16A:
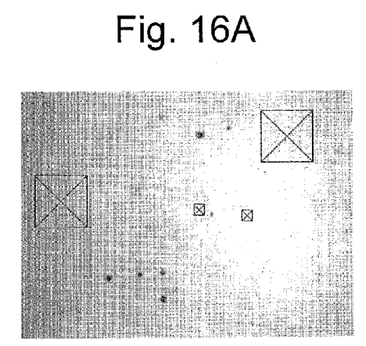
FIG. 16A is a diagram illustrating the aperture candidates set to still another observation image after the region consolidating processing.
Figure 16B:
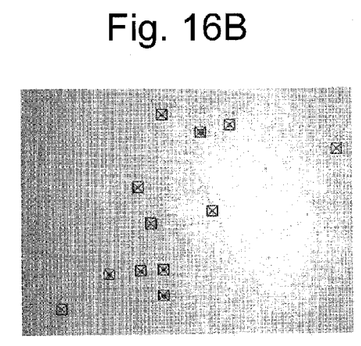
FIG. 16B is a diagram illustrating the aperture candidates set to still another observation image after the maximum point extraction.

FIG. 16A is a diagram illustrating the aperture candidates set after the region forming and consolidating processing in Steps S2 to S7, and FIG. 16B is a diagram illustrating the aperture candidates set after the maximum point extraction processing in Steps S9 and S10. In the used observation image, satin black spots emerge, but the apertures are set at portions exclusive of the black spots in the region forming and consolidating processing, and the apertures cannot be automatically set on the portions inclusive of the black spots. On the other hand, the aperture is set on each of the black spots in the maximum point extraction processing. The maximum point extraction processing is suitable for the satin sample described above.

When the maximum point extraction processing cannot be appropriately performed, as illustrated in FIG. 15B, the apertures are mainly set on the boundary portion. For this reason, when the apertures emerge side by side in a striped pattern, the controller 11 may determine that its result is inappropriate, and only the result obtained in the region forming and consolidating processing may be displayed on the display unit 13.

It is noted that the infrared microscope has been described in the embodiment, but the present invention can be applied to microspectroscopy apparatuses microscopic mass spectrometer, or the like other than the infrared microscope.

REFERENCE SIGNS LIST

1 . . . Infrared Interferometer
2 . . . Movable Stage
3 . . . Sample
4 . . . Half Mirror
5 . . . Variable Aperture 6 ... Reflective Mirror
7 ... Infrared Detector
8 ... Visible Light Source
9 ... CCD Camera
10 ... Data Processor
100 ... Fourier Transformation Calculator
11 ... Controller
12 ... Input Unit
13 ... Display Unit

The invention claimed is:

1. An analysis target region setting apparatus configured to set an analysis target region that is a region analyzed by an analyzer in an observation region of a sample; comprising:
   a pixel information acquisition means configured to acquire pixel information on each pixel constituting the observation region;
   a sub-region forming means configured to classify each pixel in accordance with the pixel information and form plural sub-regions each composed of one pixel or pixels that belong to a same classification and are adjacent to each other;
   a consolidation information calculating means configured to obtain a characteristic value regarding a part or whole of pixels in each sub-region as consolidation information; and
   a region consolidating means configured to consolidate two adjacent sub-regions of the plural sub-regions based on the consolidation information,
   wherein the region consolidating means is configured to consolidate the two adjacent sub-regions based on the number of pixels in each sub-region and a difference between a statistic of the pixel information on entire pixels in each sub-region and a statistic of the pixel information on entire pixels in a sub-region adjacent to the sub-region.

2. An analysis target region setting apparatus configured to set an analysis target region that is a region analyzed by an analyzer in an observation region of a sample; comprising:
   a pixel information acquisition means configured to acquire pixel information on each pixel constituting the observation region;
   a sub-region forming means configured to classify each pixel in accordance with the pixel information and form plural sub-regions each composed of one pixel or pixels that belong to a same classification and are adjacent to each other;
   a consolidation information calculating means configured to obtain a characteristic value regarding a part or whole of pixels in each sub-region as consolidation information; and
   a region consolidating means configured to consolidate two adjacent sub-regions of the plural sub-regions based on the consolidation information,
   wherein the region consolidating means is configured to consolidate the two adjacent sub-regions based on the number of pixels positioned on a boundary with the adjacent sub-regions and a statistic of a difference of the pixel information on adjacent pixels on the boundary, in each sub-region.

3. An analysis target region setting apparatus configured to set an analysis target region that is a region analyzed by an analyzer in an observation region of a sample; comprising:
   a pixel information acquisition means configured to acquire pixel information on each pixel constituting the observation region;
   a sub-region forming means configured to classify each pixel in accordance with the pixel information and form plural sub-regions each composed of one pixel or pixels that belong to a same classification and are adjacent to each other;
   a consolidation information calculating means configured to obtain a characteristic value regarding a part or whole of pixels in each sub-region as consolidation information; and
   a region consolidating means configured to consolidate two adjacent sub-regions of the plural sub-regions based on the consolidation information,
   wherein the region consolidating means is configured to consolidate the adjacent sub-regions based on a degree of circularity calculated from the number of pixels in each sub-region and the number of pixels on a boundary between the sub-region and neighboring sub-regions.

4. The analysis target region setting apparatus according to claim 1, further comprising a control means configured to employ the consolidation information calculating means and the region consolidating means plural times.

5. The analysis target region setting apparatus according to claim 4,
   wherein the control means is configured to make it possible to change a condition of the consolidation information provided for the region consolidating means to consolidate the two adjacent sub-regions, at a predetermined timing.

6. The analysis target region setting apparatus according to claim 1,
   wherein processing of extracting an abnormal point in the observation image is parallelly performed, and the abnormal point and each sub-region finally obtained are displayed on a predetermined display screen in a selectable manner.

7. The analysis target region setting apparatus according to claim 2, further comprising a control means configured to employ the consolidation information calculating means and the region consolidating means plural times.

8. The analysis target region setting apparatus according to claim 3, further comprising a control means configured to employ the consolidation information calculating means and the region consolidating means plural times.

9. The analysis target region setting apparatus according to claim 7,
   wherein the control means is configured to make it possible to change a condition of the consolidation information provided for the region consolidating means to consolidate the two adjacent sub-regions, at a predetermined timing.

10. The analysis target region setting apparatus according to claim 8,
    wherein the control means is configured to make it possible to change a condition of the consolidation information provided for the region consolidating means to consolidate two adjacent sub-regions, at a predetermined timing.

11. The analysis target region setting apparatus according to claim 2,
    wherein processing of extracting an abnormal point in the observation image is parallelly performed, and the abnormal point and each sub-region finally obtained are displayed on a predetermined display screen in a selectable manner.

12. The analysis target region setting apparatus according to claim 3,
wherein processing of extracting an abnormal point in the observation image is parallelly performed, and the abnormal point and each sub-region finally obtained are displayed on a predetermined display screen in a selectable manner.

13. The analysis target region setting apparatus according to claim 4,
wherein processing of extracting an abnormal point in the observation image is parallelly performed, and the abnormal point and each sub-region finally obtained are displayed on a predetermined display screen in a selectable manner.

14. The analysis target region setting apparatus according to claim 5,
wherein processing of extracting an abnormal point in the observation image is parallelly performed, and the abnormal point and each sub-region finally obtained are displayed on a predetermined display screen in a selectable manner.

15. The analysis target region setting apparatus according to claim 7,
wherein processing of extracting an abnormal point in the observation image is parallelly performed, and the abnormal point and each sub-region finally obtained are displayed on a predetermined display screen in a selectable manner.

16. The analysis target region setting apparatus according to claim 8,
wherein processing of extracting an abnormal point in the observation image is parallelly performed, and the abnormal point and each sub-region finally obtained are displayed on a predetermined display screen in a selectable manner.

17. The analysis target region setting apparatus according to claim 9,
wherein processing of extracting an abnormal point in the observation image is parallelly performed, and the abnormal point and each sub-region finally obtained are displayed on a predetermined display screen in a selectable manner.

18. The analysis target region setting apparatus according to claim 10,
wherein processing of extracting an abnormal point in the observation image is parallelly performed, and the abnormal point and each sub-region finally obtained are displayed on a predetermined display screen in a selectable manner.

* * * * *